United States Patent
Chan et al.

(10) Patent No.: US 11,779,295 B2
(45) Date of Patent: Oct. 10, 2023

(54) METHOD AND SYSTEM OF VERTEBRAL COMPRESSION FRACTURE DETECTION

(71) Applicants: Quanta Computer Inc., Taoyuan (TW); Taipei Medical University, Taipei (TW)

(72) Inventors: Wing P. Chan, Taipei (TW); Ai-Ling Hsu, Taoyuan (TW); Kuan-Chieh Huang, Taoyuan (TW); Yi-Ting Peng, Taoyuan (TW); Ching-Chung Kao, Taoyuan (TW)

(73) Assignees: QUANTA COMPUTER INC., Taoyuan (TW); TAIPEI MEDICAL UNIVERSITY, Taipei (TW)

( * ) Notice: Subject to any disclaimer, the term of this patent is extended or adjusted under 35 U.S.C. 154(b) by 280 days.

(21) Appl. No.: 17/223,605

(22) Filed: Apr. 6, 2021

(65) Prior Publication Data

US 2021/0378616 A1 Dec. 9, 2021

(30) Foreign Application Priority Data

Jun. 9, 2020 (TW) ................................. 109119248

(51) Int. Cl.
*A61B 6/00* (2006.01)
*G06T 7/00* (2017.01)
*A61B 6/03* (2006.01)

(52) U.S. Cl.
CPC .............. *A61B 6/5223* (2013.01); *A61B 6/03* (2013.01); *A61B 6/468* (2013.01); *A61B 6/505* (2013.01);

(Continued)

(58) Field of Classification Search
CPC ......... A61B 6/5223; A61B 6/03; A61B 6/468; A61B 6/505; A61B 6/5229; A61B 6/032;
(Continued)

(56) References Cited

U.S. PATENT DOCUMENTS

2015/0363963 A1* 12/2015 Zhan ...................... G06T 7/149
600/410
2019/0251694 A1* 8/2019 Han ...................... G06T 3/0068

OTHER PUBLICATIONS

Bar, A., et al.; "Compression fractures detection on CT;" Proc. SPIE 10134, Medical Imaging 2017: Computer-Aided Diagnosis; Jun. 2017; pp. 1-8.

(Continued)

*Primary Examiner* — Siamak Harandi
(74) *Attorney, Agent, or Firm* — McClure, Qualey & Rodack, LLP

(57) ABSTRACT

The present invention discloses a method and a system of vertebral compression fracture detection. The method of vertebral compression fracture detection includes: recombining a plurality of anatomical images captured in at least a spine segment of a target individual into a 3D image; using a multi-planar reconstruction method to reformat the 3D image to obtain at least one sagittal reformatted image; using a classification model to determine whether the sagittal reformatted image covers the middle section of the vertebral column or not; using a vertebral detection method to detect each vertebral body in the sagittal reformatted image covering the middle section of the vertebral column; using a keypoint localization method to localize a plurality of keypoints of each vertebral body which was detected in the sagittal reformatted image; evaluating the compression fracture grade of each vertebral body in the sagittal reformatted image.

9 Claims, 16 Drawing Sheets

(52) U.S. Cl.
CPC .......... *A61B 6/5229* (2013.01); *G06T 7/0012* (2013.01); *G06T 2207/10028* (2013.01); *G06T 2207/20081* (2013.01); *G06T 2207/20084* (2013.01); *G06T 2207/30012* (2013.01)

(58) Field of Classification Search
CPC ................ A61B 6/5217; G06T 7/0012; G06T 2207/10028; G06T 2207/20081; G06T 2207/20084; G06T 2207/30012; G06T 2207/10081
See application file for complete search history.

(56) References Cited

OTHER PUBLICATIONS

Nicolaes, J., et al.; "Detection of Vertebral Fractures in CT Using 3D Convolutional Neural Networks;" International Workshop and Challenge on Computational Methods and Clinical Applications for Spine Imaging CSI 2019: Computational Methods and Clinical Applications for Spine Imaging; Nov. 2019; pp. 1-13.

* cited by examiner

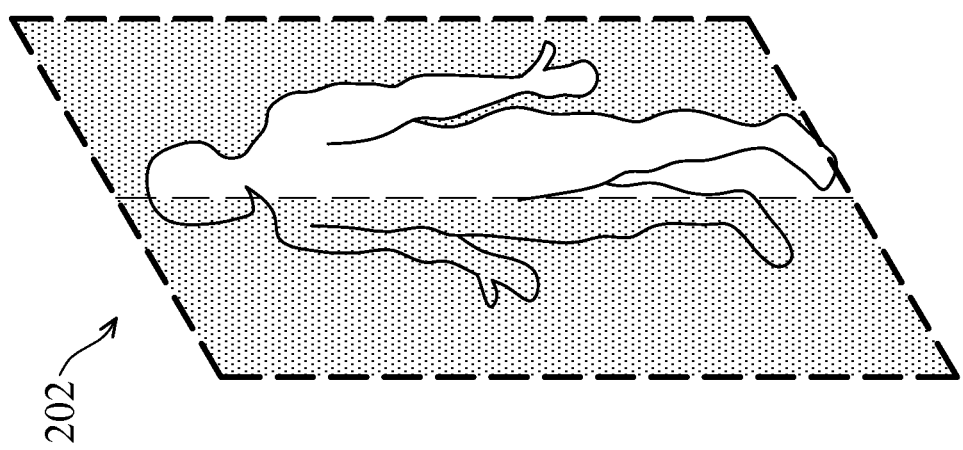
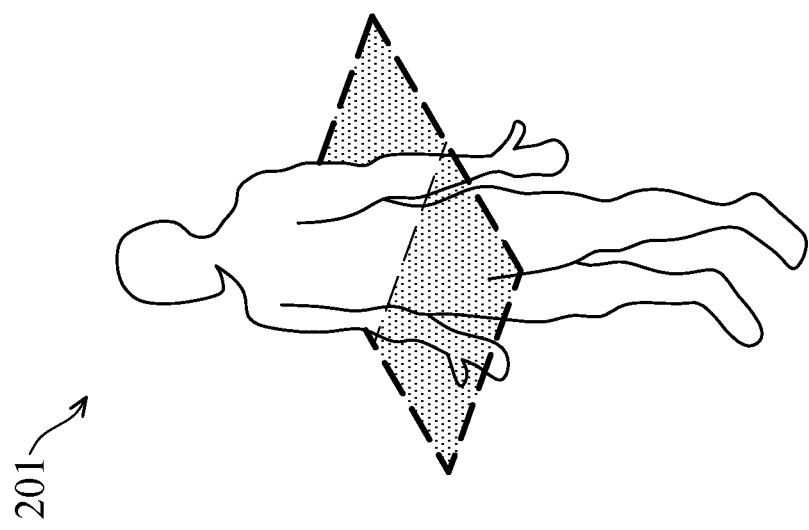
FIG. 2

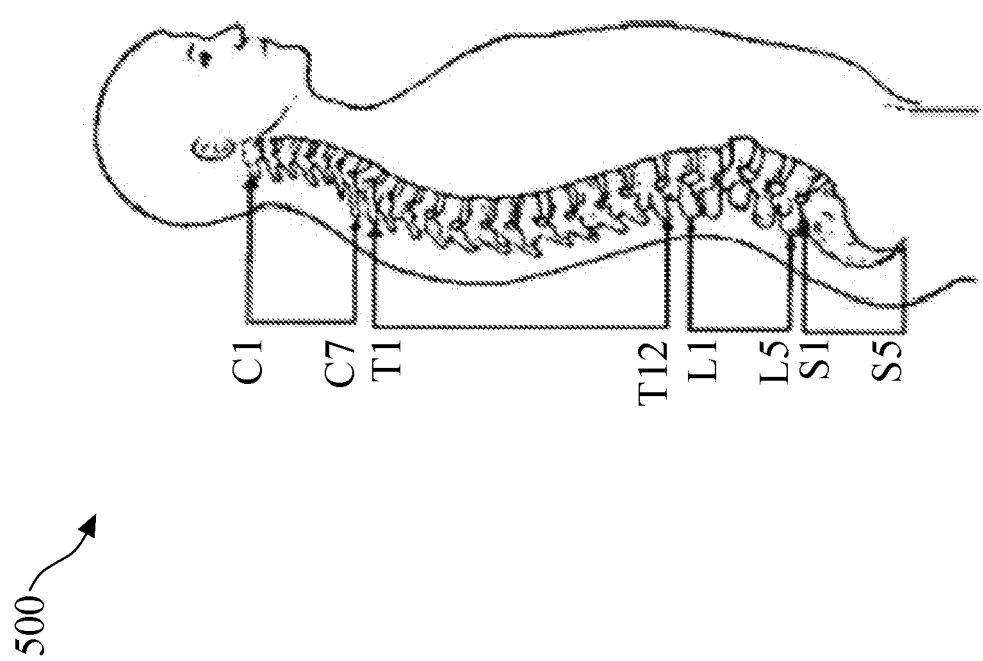

METHOD AND SYSTEM OF VERTEBRAL COMPRESSION FRACTURE DETECTION

CROSS REFERENCE TO RELATED APPLICATIONS

This application claims priority of Taiwan Patent Application No. 109119248, filed on Jun. 9, 2020, the entirety of which is incorporated by reference herein.

BACKGROUND OF THE INVENTION

Field of the Invention

The present invention relates to a method and a system of vertebral compression fracture detection, and, in particular, to a method and a system of vertebral compression fracture detection which uses a plurality of anatomical images captured in at least a spine segment of a target individual as input to perform the steps of recombining, reformatting, classifying, detecting and localizing, and evaluating the compression fracture grade according to the result of localization.

Description of the Related Art

With the quality improvement in healthcare, life expectancy around the world has increased. Falls, however, are the leading causes of injury-related death among the elderly. For the elderly, the risk of hip fracture and death caused by falling is much more pronounced than it is for the younger population. According to statistics from the National Health Insurance Administration of Taiwan, the one-year mortality rate of elderly patients with hip fracture is 11% higher than the standardized mortality rate of those without hip fracture. Especially in elderly females, asymptomatic vertebral compression fracture (VCF) is an indicator of a subsequent hip fracture. The Consensus and Guideline on the Prevention of Adult in Taiwan published in 2017 shows that the incidence rate of VCF for Taiwanese elderly is 16.2%, which accounts for approximately 482,000 patients. Despite its high prevalence and serious consequences, the majority of vertebral fractures are frequently underreported and thus potentially delay the treatment. Notwithstanding the low preventive screening rate of vertebral fracture, clinicians may still diagnose a VCF based on routine Computerized Tomography (CT) scan targeting at the thoracic, abdominal, or pelvis portions including vertebrae.

Focusing on the patients aged over 50 years with hip fracture, Mitchell et al. (*Archives of Osteoporosis*, 2017) showed that 157 out of 732 patients had radiological imaging covering the spine in the previous 6 years; however, only 30 from 65 cases with a compression fracture were accurately reported, highlighting an under-reporting rate up to 54% (35/65). One of the potential factors for the high under-reporting rate of VCF is that the clinical CT images are natively acquired in the axial plane, which is suboptimal for clinicians to assess the height reduction of vertebral bodies for VCF diagnosis. Despite being available on most of the acquired axial images, performing sagittal reformation to obtain the optimal images for VCF diagnosis is frequently ignored in clinical routines. This invention addresses the need to develop a new automatic system for VCF screening through clinical CT scans in order to counter the under-reporting rate of VCF and the patient's unawareness to screen for this disease.

BRIEF SUMMARY OF THE INVENTION

In view of the limitations of the prior art, the present invention is intended to provide a method and a system for VCF detection, which uses anatomical images acquired as inputs to perform the steps of recombining, reformatting, classifying, detecting, localizing, and evaluating the compression fracture grade according to the result of localization.

An embodiment of the present invention discloses a method of VCF detection, including: recombining a plurality of anatomical images captured in at least a spine segment of a target individual into a 3D image; using a multi-planar reconstruction method to reformat the 3D image to obtain at least one sagittal reformatted image; using a classification method to determine whether the sagittal reformatted image covers the middle section of the vertebral column or not; using a vertebral detection method to detect each vertebral body in the sagittal reformatted image covering the middle section of the vertebral column; using a keypoint localization method to localize a plurality of keypoints of each vertebral body which was detected in the sagittal reformatted image; evaluating the compression fracture grade of each vertebral body in the sagittal reformatted image based on the result of keypoint localization.

The classification method disclosed by the embodiment of the present invention uses a trained deep-learning classification model to determine whether the sagittal reformatted image covers the middle section of the vertebral column or not; wherein the input data required by the training process of the deep-learning classification model are a plurality of sagittal reformatted images with annotation (the middle or non-middle section of the vertebral column) by medical domain professionals (e.g., doctors, radiologists or researchers).

The vertebral detection method disclosed by the embodiment of the present invention uses a trained deep-learning detection model to detect each vertebral body in the sagittal reformatted image; wherein the input data required by the training process of the deep-learning detection model are a plurality of sagittal reformatted images in which each vertebral body is annotated by medical domain professionals.

The keypoint localization method disclosed by the embodiment of the present invention uses a trained deep-learning keypoint localization model to localize keypoints of each vertebral body; wherein the input data required by the training process of the deep-learning keypoint localization model are a plurality of sagittal reformatted images in which the keypoints of each vertebral body are annotated by medical domain professionals.

An embodiment of the present invention discloses a system of VCF detection, including an electronic device, including a processing device, for loading programs and performing the method as described above.

In some embodiments, the system of VCF detection further includes a storage device, storing CT scans and patients' basic information as a specific-format file, and transferring the specific-format file to the electronic device; the electronic device receives the specific-format file from the storage device, deconstructs the specific-format file into metadata and image data, and uses the image data as input to perform the method as described above.

In some embodiments, the processing device of the system of VCF detection may further be configured to perform a demonstration method to overlay the localization result of the vertebral keypoints and the evaluation result of the compression fracture grade for each vertebral body in the sagittal reformatted image.

In some embodiments, the system of VCF detection further includes a display device, providing a user interface to demonstrate the sagittal reformatted image overlaid with the localization result and the corresponding compression fracture grade for each vertebral body, and allow medical domain professionals to revise the localization result of each vertebral body on the user interface.

In some embodiments, the processing device of the system of VCF detection may further be configured to perform a keypoint refinement method, including: using a trained deep-learning joint-keypoint refinement model to automatically refine the location of the rest of unrevised keypoints after either one or few keypoints of a vertebra are corrected manually by the medical domain professionals; updating the corresponding compression fracture grade of the vertebral body in the sagittal reformatted image, based on the result of the trained deep-learning joint-keypoint refinement model; wherein the input data required by the training process of the deep-learning joint-keypoint refinement model are a plurality of sagittal reformatted images in which the keypoints of each vertebral body are annotated by medical domain professionals.

BRIEF DESCRIPTION OF THE DRAWINGS

The present invention can be more fully understood by reading the subsequent detailed description and examples with references made to the accompanying drawings, wherein:

FIG. 2 illustrates an anatomical image obtained from an axial plane and a sagittal plane of a target individual in which the present application may be implemented.

FIG. 5 is an illustration of vertebral structure which is well-known and commonly used in the medical field.

DETAILED DESCRIPTION OF THE INVENTION

The following description is made for the purpose of illustrating the general principles of the invention and should not be taken in a limiting sense. The scope of the invention is best determined by reference to the appended claims.

Figure 1:
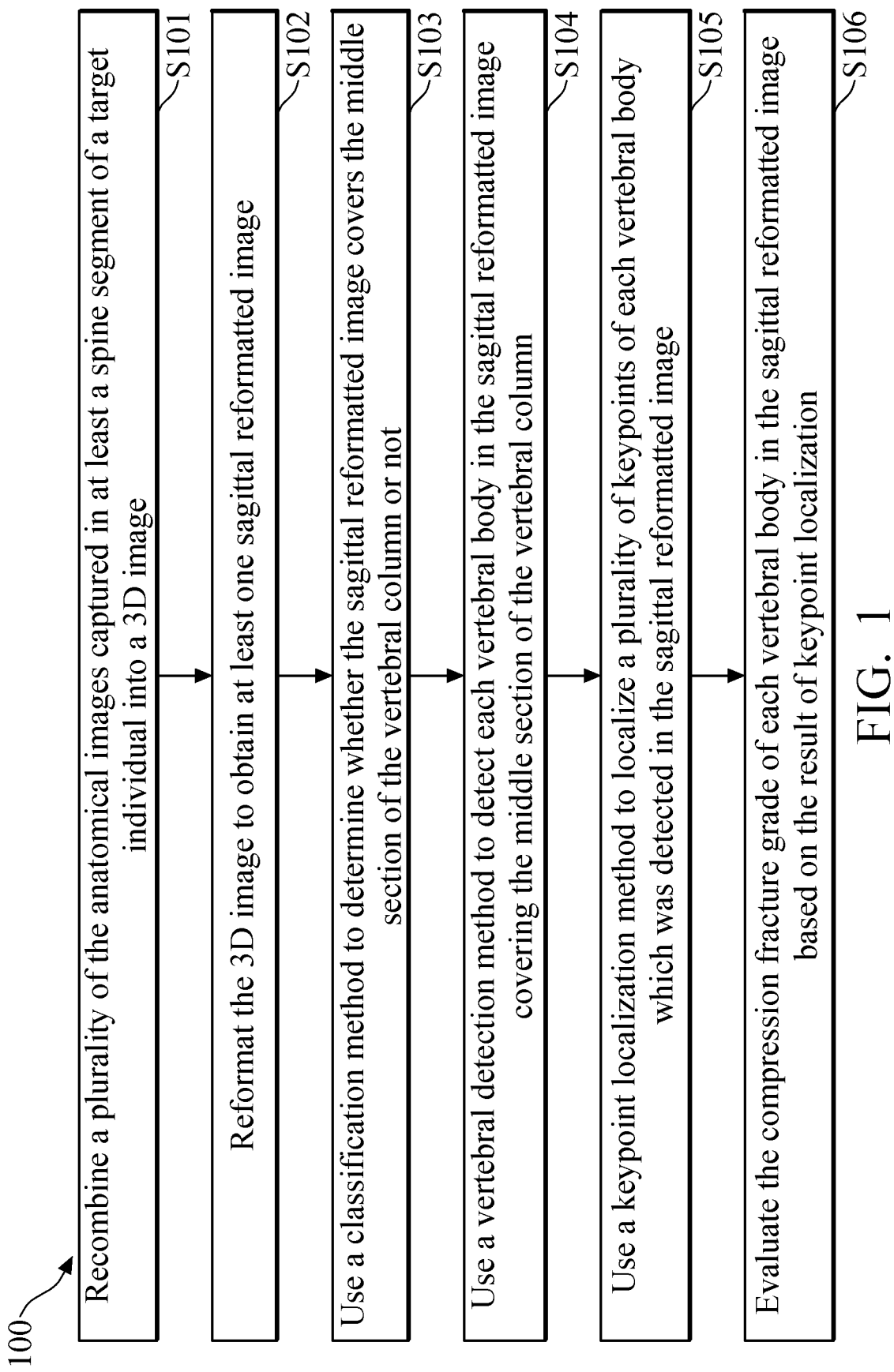
FIG. 1 is the flow diagram showing a method for detecting VCF in a set of anatomical images in which the present application may be implemented.

FIG. 1 is the flow diagram showing a method for detecting VCF in a set of anatomical images in which the present application may be implemented. VCF detection method 100, a method for detecting VCF in a set of anatomical images, includes steps S101-S106. First, in step S101, recombine a plurality of anatomical images captured in at least a spine segment of a target individual into a 3D image, and then proceed to S102. In step S102, reformat the 3D image to obtain at least one sagittal reformatted image, and then proceed to S103. In step S103, use a classification method to determine whether the sagittal reformatted image covers the middle section of the vertebral column or not, and then proceed to S104. In step S104, use a vertebral detection method to detect each vertebral body in the sagittal reformatted image covering the middle section of the vertebral column, and then proceed to S105. In step S105, use a keypoint localization method to localize a plurality of keypoints of each vertebral body which was detected in the sagittal reformatted image, and then proceed to S106. In step S106, evaluate the compression fracture grade of each vertebral body in the sagittal reformatted image based on the result of keypoint localization.

FIG. 2 illustrates an anatomical image obtained from an axial plane and a sagittal plane of a target individual, according to the embodiment of the present application. As illustrated in FIG. 2, anatomical image 201 is obtained from a horizontal plane of a target individual that is perpendicular to the long axis of the human body and used to divide the human body into superior and inferior parts. Sagittal reformatted image 202 is obtained from a longitudinal plane of a target individual that is parallel to the long axis of the human body and used to divide the human body into left and right sides.

In some embodiments of the present invention, S101 in FIG. 1 is to recombine a plurality of anatomical images 201 captured in at least a spine segment of a target individual into a 3D image. The number of anatomical images 201 is determined by the region of the CT scan taken by the patient. The region of the CT scan may be, for example, the thorax, abdomen, or pelvis. The intention of acquiring the CT scan is to capture the target regions, whereas the spatial coverage of the scan captures the vertebra as well; thus, the 3D image recombined from the CT scan covering the target regions may cover the vertebra.

In some embodiments of the present invention, S102 in FIG. 1 is to reformat the 3D image which is the result of the S101, and obtain at least one sagittal reformatted image 202.

Figure 3A:
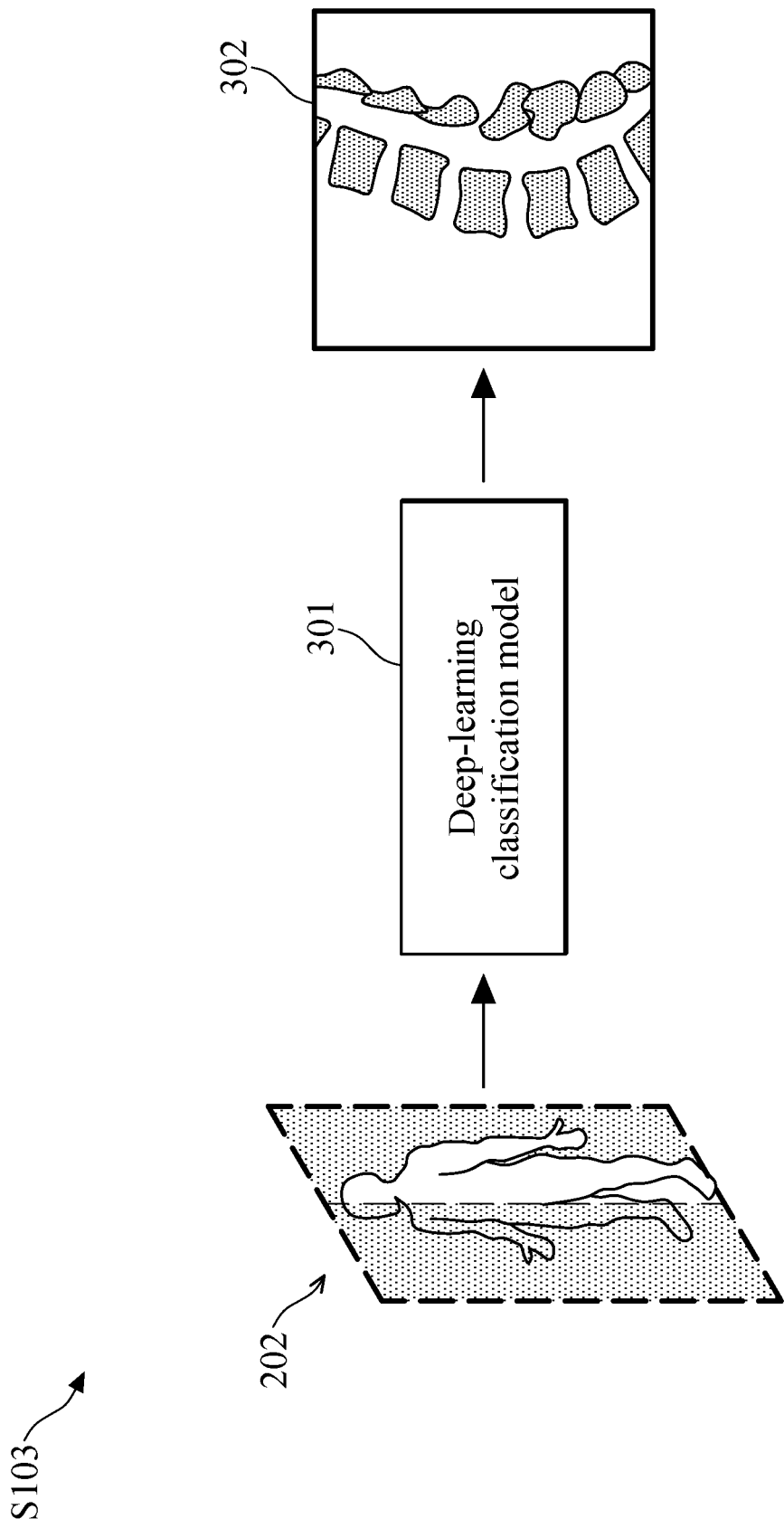
FIG. 3A is the block diagram for determination of a sagittal reformatted image in the middle or non-middle section of the vertebral column, according to the embodiment of the present application.

FIG. 3A is the block diagram of step S103 in FIG. 1 for determining whether a sagittal reformatted image covers the middle of the vertebral column or not, according to the embodiment of the present application. As illustrated in FIG. 3A, S103 is to feed the sagittal reformatted image 202 generated by S102 into a trained deep-learning classification model 301, and then determine whether the sagittal reformatted image 202 covers the middle section of the vertebral column or not, and reserve the sagittal reformatted images covering the middle section of the vertebral column 302. In some embodiments, the sagittal reformatted image in the middle section of the vertebral column means to present all vertebral bodies within the middle section of the vertebral column in the sagittal reformatted image.

Figure 3B:
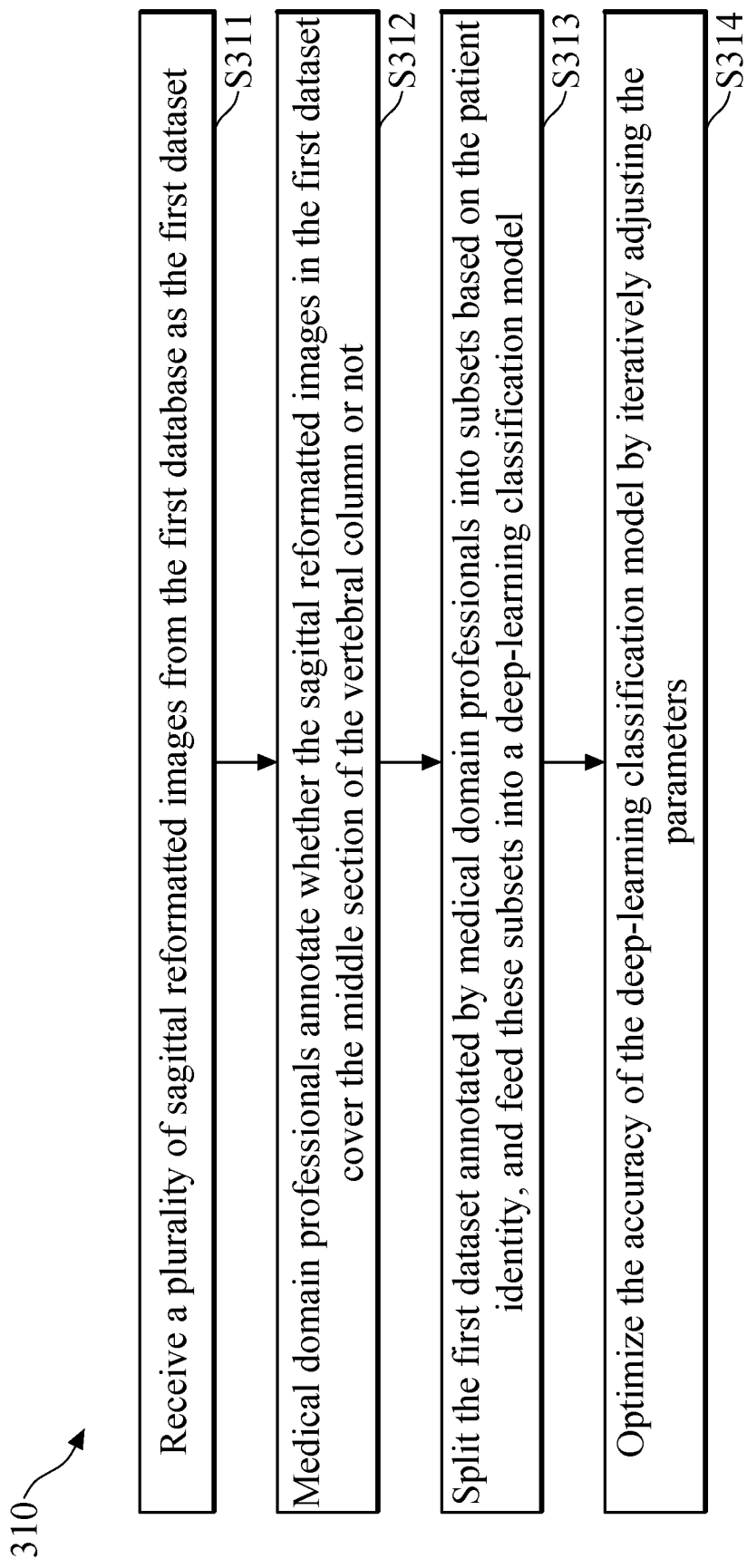
FIG. 3B is the flow diagram showing the training process of a deep-learning classification model, according to the embodiment of the present application.

FIG. 3B is the flow diagram showing the training process 310 of the trained deep-learning classification model 301, according to the embodiment of the present application. The training process 310 of the trained deep-learning classification model 301 includes steps S311-S314. First, in step S311, receive a plurality of sagittal reformatted images from the first database as the first dataset, and then perform step S312. In step S312, medical domain professionals annotate whether the sagittal reformatted images in the first dataset cover the middle section of the vertebral column or not, and then perform step S313. In step S313, split the first dataset annotated by medical domain professionals into subsets based on the patient identity, and feed these subsets into a deep-learning classification model, and then perform step S314. In step S314, optimize the accuracy of the deep-learning classification model by iteratively adjusting the parameters; after performing the steps described above, generate the trained deep-learning classification model 301 which is capable of determining whether a sagittal reformatted image covers the middle section of the vertebral column or not.

In some embodiments, in step S311, the first dataset may be, for example, the database from the retrospective CT scans and the corresponding clinical reports, wherein the database includes sagittal reformatted images in both middle section and non-middle section of the vertebral column from patients with compression fractures and that without compression fractures.

In some embodiments, in step S313, the first dataset may be split into three subsets, the training dataset, the validation dataset, and the testing dataset, for training the deep-learning model, selecting the final model, and evaluating the accuracy of the model, respectively.

In some embodiments, in step S313, the deep-learning classification model may be, for example, fine-tuned or modified from a variety of convolutional neural network (CNN) based image classification models, such as GoogLeNet, ResNet, InceptionResNet, etc.

In some embodiments, if the sagittal reformatted image 202 contains implants or imaging artifacts caused by the implants, the detection and analysis of compression fractures may be stopped. Therefore, the step S103 in FIG. 1 may not only determine whether the sagittal reformatted image 202 is located in the middle section of the vertebral column or not, but may also determine whether the sagittal reformatted image 202 contains implants or imaging artifacts caused by the implants.

Figure 4A:
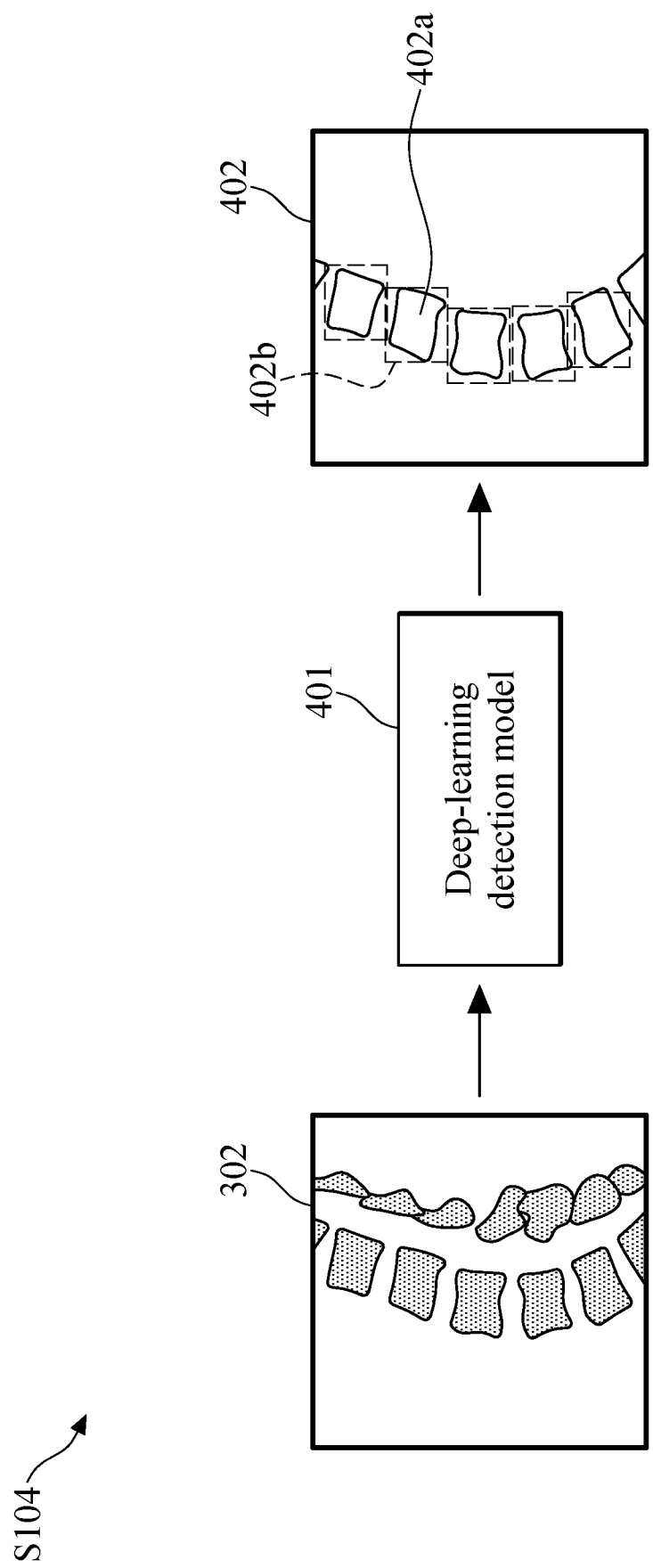
FIG. 4A is the block diagram for detection of vertebral bodies in a sagittal reformatted image, according to the embodiment of the present application.

FIG. 4A is the block diagram of step S104 in FIG. 1 for detection of vertebral bodies in a sagittal reformatted image, according to the embodiment of the present application. As illustrated in FIG. 4A, S104 is to feed the sagittal reformatted image located in the middle section of the vertebral column 302 into a trained deep-learning detection model 401, and then generate the detection result 402. Detection result 402 includes a plurality of vertebral body segments 402a and a plurality of vertebral body bounding boxes 402b. The bounding boxes 402b are a plurality of rectangular boxes surround the vertebral body segments 402a, and the specific format of bounding boxes 402b may be, for example, the coordinate of a reference point (e.g., the upper left point of a bounding box) in the images and the length and width of a bounding box 402b with respect to the reference point. In other words, the detection result 402 of an image is demonstrated by a plurality of vertebral body segments 402a but implemented by a plurality of bounding boxes 402b.

Figure 4B:
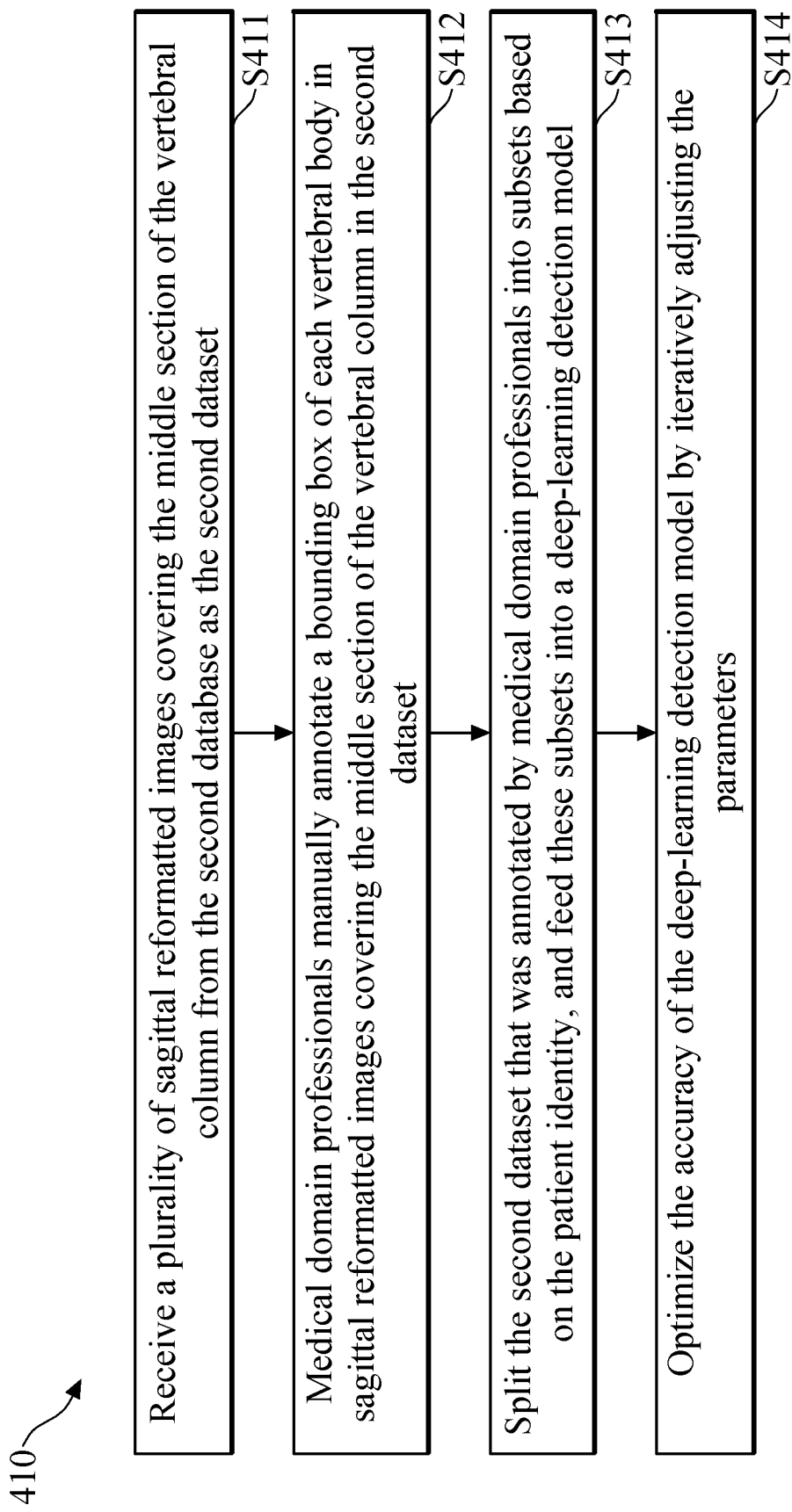
FIG. 4B is the flow diagram showing the training process of a deep-learning detection model, according to the embodiment of the present application.

FIG. 4B is the flow diagram showing the training process 410 of the trained deep-learning detection model 401, according to the embodiment of the present application. The training process 410 of the trained deep-learning detection model 401 includes steps S411-S414. First, in step S411, receive a plurality of sagittal reformatted images covering the middle section of the vertebral column from the second database as the second dataset, and then perform step S412. In step S412, medical domain professionals manually annotate a bounding box of each vertebral body in sagittal reformatted images covering the middle section of the vertebral column in the second dataset, and then perform step S413. In step S413, split the second dataset that was annotated by medical domain professionals (vertebrae were annotated using bounding boxes as presented in the detection result 402 in FIG. 4A) into subsets based on the patient identity, and feed these subsets into a deep-learning detection model, and then perform step S414. In step S414, optimize the accuracy of the deep-learning detection model by iteratively adjusting the parameters; after performing the steps described above, generate the trained deep-learning detection model 401 which is capable of detecting each vertebral body in a sagittal reformatted image covering the middle section of the vertebral column.

In some embodiments, in step S411, the second dataset may be, for example, the database from retrospective CT scans and the corresponding clinical reports, wherein the database includes sagittal reformatted images in both middle section and non-middle section of the vertebral column from patients with compression fractures and that without compression fractures.

In some embodiments, in step S413, the second dataset may be split into three subsets, the training dataset, the validation dataset, and the testing dataset, for training the deep-learning model, selecting the final model, and evaluating the accuracy of the model, respectively.

In some embodiments, in step S413, the deep-learning detection model may be, for example, fine-tuned or modified from a variety of CNN based object detection models, such as an SSD (Single Shot MultiBox Detector), YOLO (You Only Look Once), Faster-RCNN (Region-based Convolutional Neural Networks), Mask-RCNN, etc.

FIG. 5 is an illustration of vertebral structure 500 which is well-known and commonly used in the medical field. In some embodiments, the deep-learning classification model described above may be adopted to recognize each vertebral body in detection result 402, such as the $12^{th}$ thoracic vertebra (T12 in vertebral structure 500), $1^{st}$ lumber vertebra (L1 in vertebral structure 500), $5^{th}$ lumber vertebra (L5 in vertebral structure 500), etc.

Figure 6A:
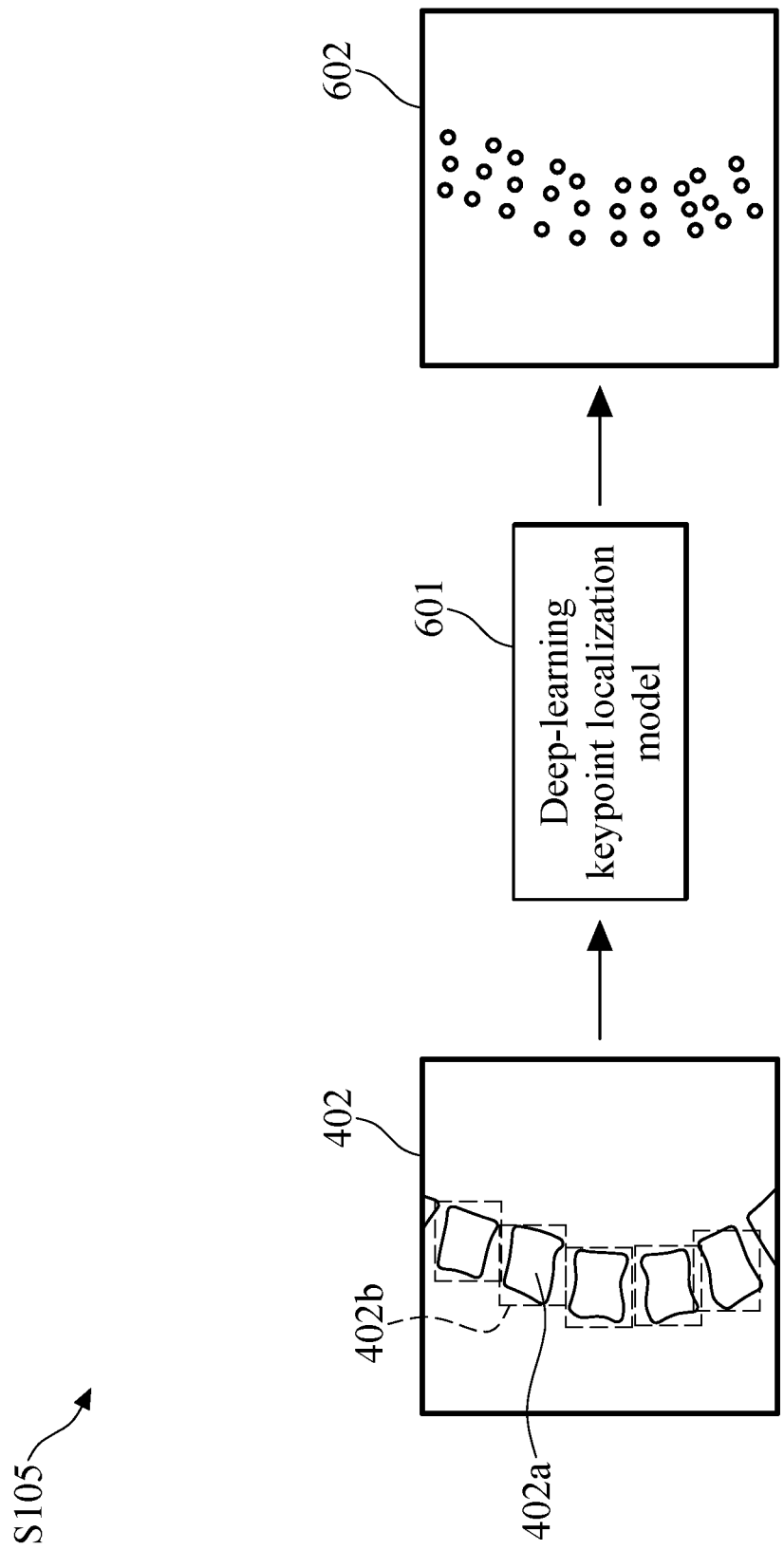
FIG. 6A is the block diagram for keypoint localization of each vertebral body in a sagittal reformatted image, according to the embodiment of the present application.

FIG. 6A is the block diagram of step S105 in FIG. 1 for keypoint localization of each vertebral body in a sagittal reformatted image, according to the embodiment of the present application. As illustrated in FIG. 6A, step S105 is to feed detection result 402 into the trained deep-learning keypoint localization model 601, and then generate the localization result 602.

Figure 6B:
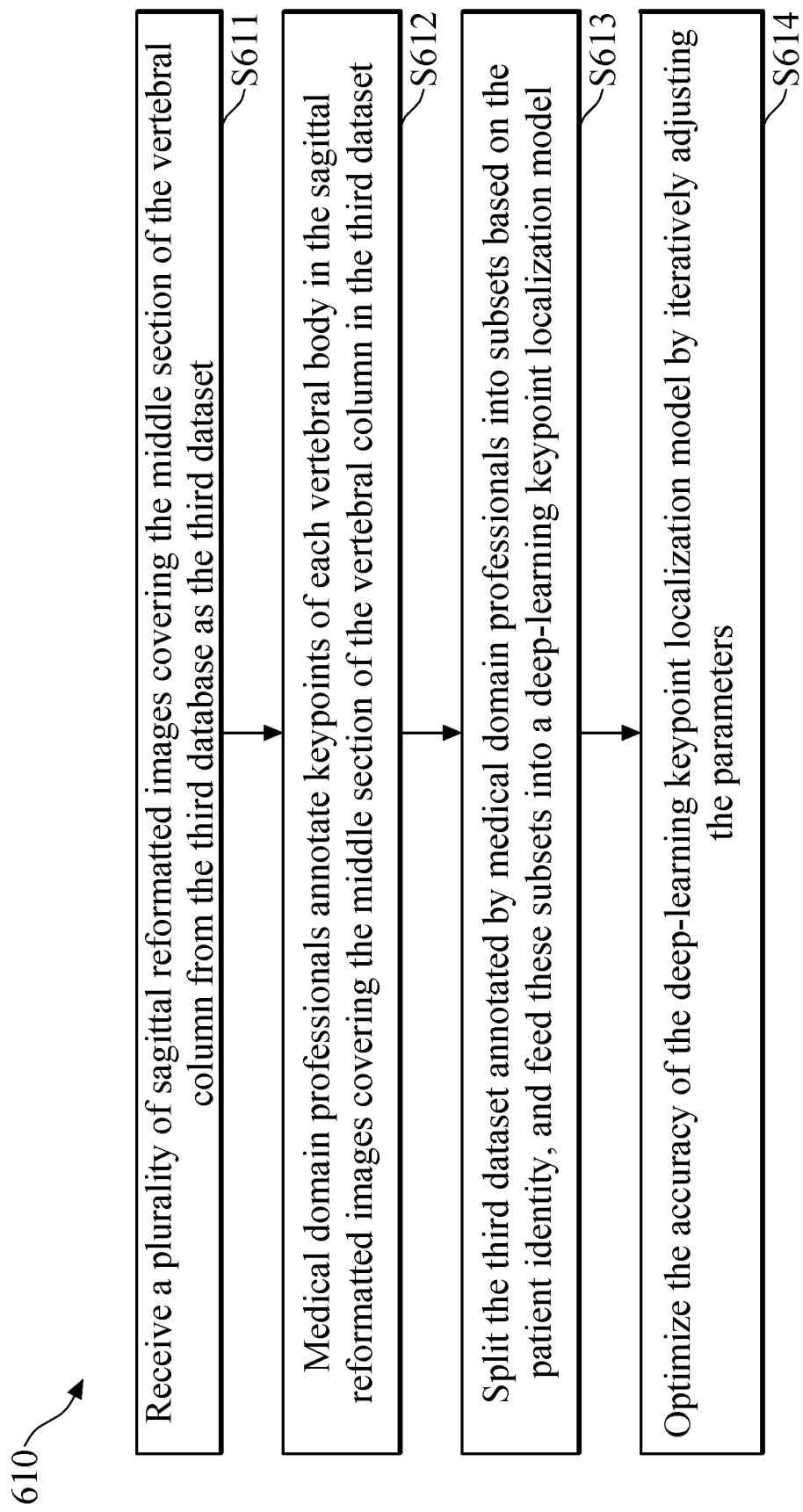
FIG. 6B is the flow diagram showing the training process of a deep-learning keypoint localization model, according to the embodiment of the present application.

FIG. 6B is the flow diagram showing the training process 610 of a deep-learning keypoint localization model 601, according to the embodiment of the present application. The training process 610 of the trained deep-learning keypoint localization model 601 includes steps S611-S614. First, in step S611, receive a plurality of sagittal reformatted images covering the middle section of the vertebral column from the third database as the third dataset, and then perform step S612. In step S612, medical domain professionals annotate keypoints of each vertebral body in the sagittal reformatted images covering the middle section of the vertebral column in the third dataset, and then perform step S613. In step S613, split the third dataset annotated by medical domain professionals into subsets based on the patient identity, and feed these subsets into a deep-learning keypoint localization model, and then perform step S614. In step S614, optimize the accuracy of the deep-learning keypoint localization model by iteratively adjusting the parameters; after performing the steps described above, generate the trained deep-learning keypoint localization model 601 which is capable of localizing the keypoints of each vertebral body.

In some embodiments, in step S611, the third dataset may be, for example, the database from the retrospective CT scans and the corresponding clinical reports, wherein the database includes sagittal reformatted images in both middle section of the vertebral column from patients with compression fractures and that without compression fractures.

In some embodiments, the first database, the second database and the third database described above may be the same database.

In some embodiments, in step S613, the third dataset may be split into three subsets, the training dataset, the validation dataset, and the testing dataset, for training the deep-learning model, selecting the final model, and evaluating the accuracy of the model, respectively.

In some embodiments, in step S613, the deep-learning keypoint localization model may be based on, for example, a regression analysis model, image segmentation model, Mask-RCNN (Region-based Convolutional Neural Networks), CPM (Convolutional Pose Machines), Keypoint RCNN, etc. The training process targets on minimizing the localization error between the keypoints localized by the model and the keypoints annotated by medical domain professionals, and the accuracy of the model is optimized through the iterative process of adjusting the model parameters.

Figure 6C:
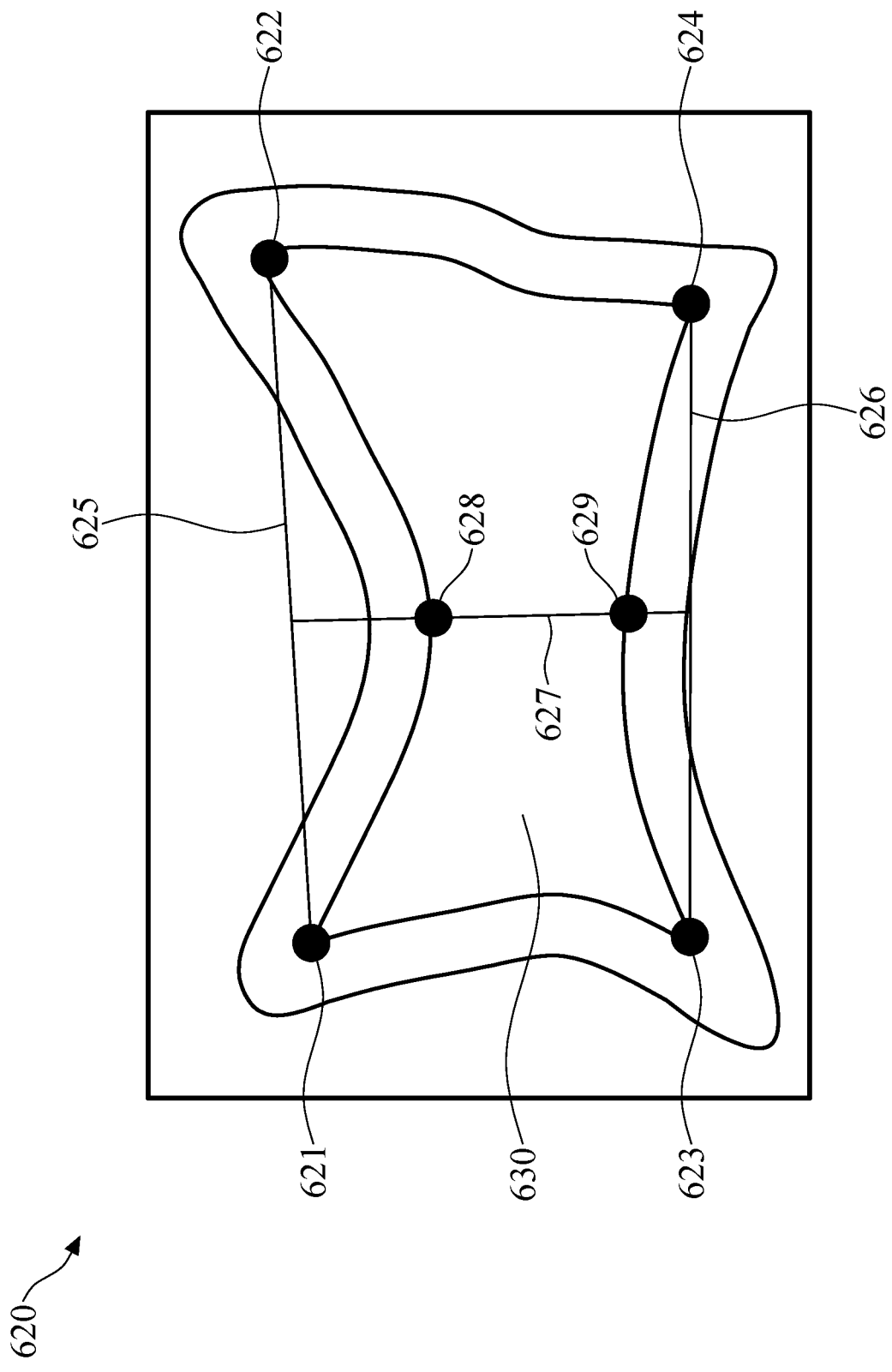
FIG. 6C illustrates a keypoint localization method for the placement of keypoints of a vertebral body in an anatomical image of a sagittal plane.

FIG. 6C illustrates the keypoint localization method 620 that places keypoint of a vertebral body in an anatomical image of a sagittal plane, according to the preferred embodiment of the present application. In the preferred embodiment, the number of localized keypoints of each vertebral body is six, and the positions of them are anterior-superior, anterior-inferior, middle-superior, middle-inferior, posterior-superior, and posterior-inferior. As illustrated in FIG. 6C, the order of the six keypoints of the vertebral body 630 (for both annotation by medical domain professionals and the prediction based on the deep-learning keypoint localization model) is anterior-superior keypoint 621, posterior-superior keypoints 622, anterior-inferior keypoints 623 and posterior-inferior keypoint 624 at the four corners of vertebral body 630; next, anterior-superior keypoint 621 and posterior-superior keypoint 622 are connected to produce superior-line-segment 625; similarly, anterior-inferior keypoint 623 and posterior-inferior keypoint 624 are connected to produce inferior-line-segment 626; then the midpoint of superior-line-segment 625 and the midpoint of inferior-line-segment 626 are connected to produce mid-line-segment 627; finally, the two points crossed by mid-line-segment 627 and the edge contour of vertebral body 630, i.e. middle-superior point 628 and middle-inferior point 629, are generated.

Figure 7:
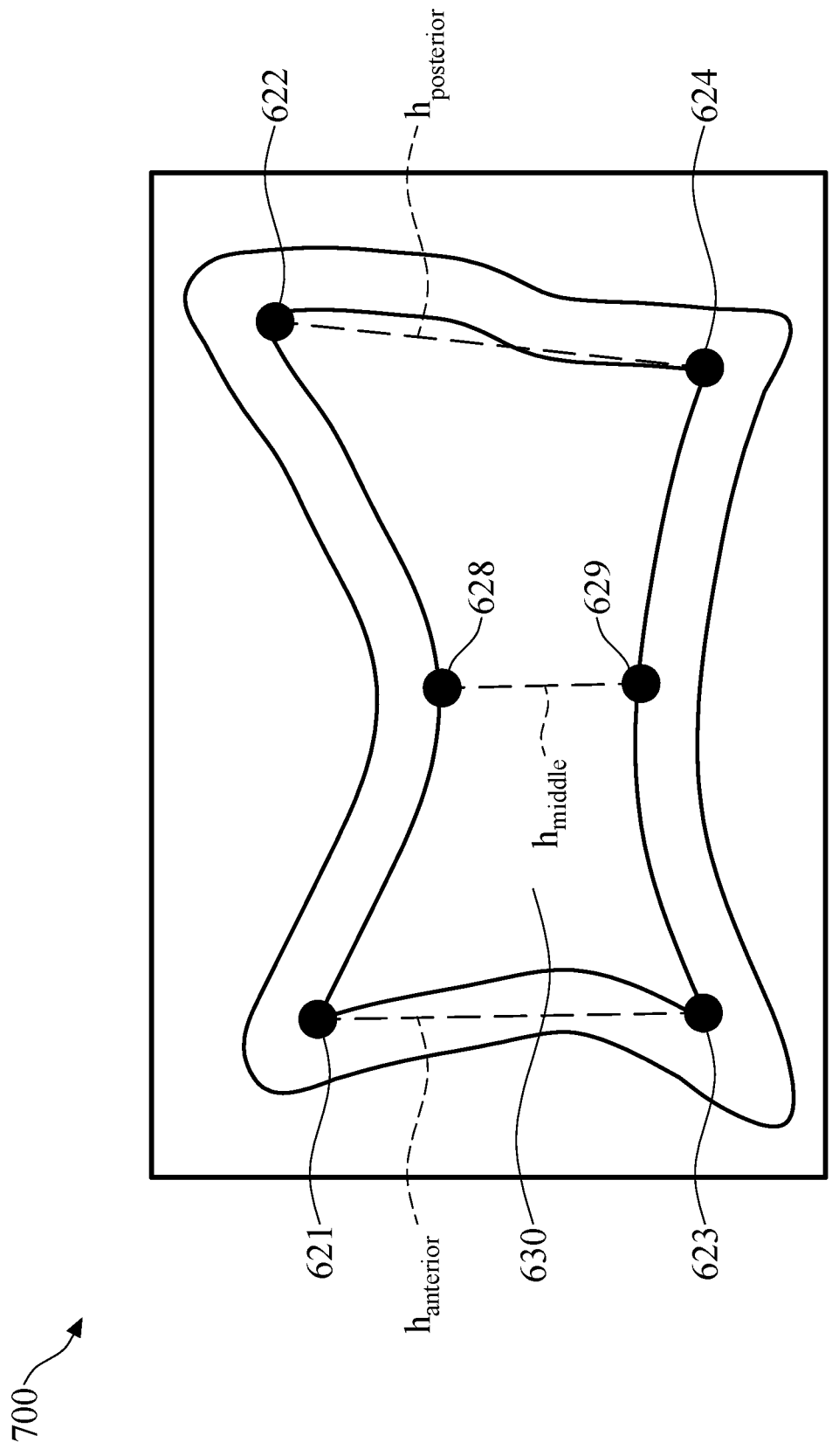
FIG. 7 illustrates an exemplary evaluation method of VCF, according to the embodiment of the present application.

FIG. 7 illustrates an exemplary evaluation method 700 of VCF adopted by step S106 in FIG. 1, according to the embodiment of the present application. In this embodiment, measure the anterior vertebral height $h_{anterior}$ between anterior-superior keypoint 621 and anterior-inferior keypoint 623, the middle vertebral height $h_{middle}$ between middle-superior keypoint 628 and middle-inferior keypoint 629, the posterior vertebral height $h_{posterior}$ between posterior-superior keypoint 622 and posterior-inferior keypoint 624, as well as the posterior-adjacent vertebral height $h_{posterior-adjacent}$ (not shown in FIG. 7) between the posterior-superior keypoint and the posterior-inferior keypoint of an adjacent vertebral body, and then substitute $h_{anterior}$, $h_{middle}$, $h_{posterior}$, and $h_{posterior-adjacent}$ into the formulas below to calculate the height-reduction ratio A and height ratio B-D of the vertebral body 630.

$$\text{Ratio } A = 1 - \frac{\min(h_{anterior}, h_{middle}, h_{posterior})}{\max(h_{anterior}, h_{middle}, h_{posterior})}$$

$$\text{Ratio } B = \frac{h_{anterior}}{h_{posterior}}$$

$$\text{Ratio } C = \frac{h_{middle}}{h_{posterior}}$$

$$\text{Ratio } D = \frac{h_{posterior}}{h_{posterior-adjacent}}$$

In the preferred embodiment, the height-reduction ratio A of each vertebral body may further be graded with respect to the Genant's criteria. To be specific, Genant's criteria currently has four grades:
Grade 0 (Normal): Height-reduction ratio is below 20%.
Grade 1 (Mild): Height-reduction ratio is greater than or equal to 20%, and below 25%.
Grade 2 (Moderate): Height-reduction ratio is greater than or equal to 25%, and below 40%.
Grade 3 (Severe): Height-reduction ratio is greater than or equal to 40%.

In some embodiments, when at least one of height-reduction ratio B-D of the vertebral body 630 is 15% higher or 3 standard deviations higher than the normative data, vertebral body 630 is determined to have compression fracture.

Figure 8A:
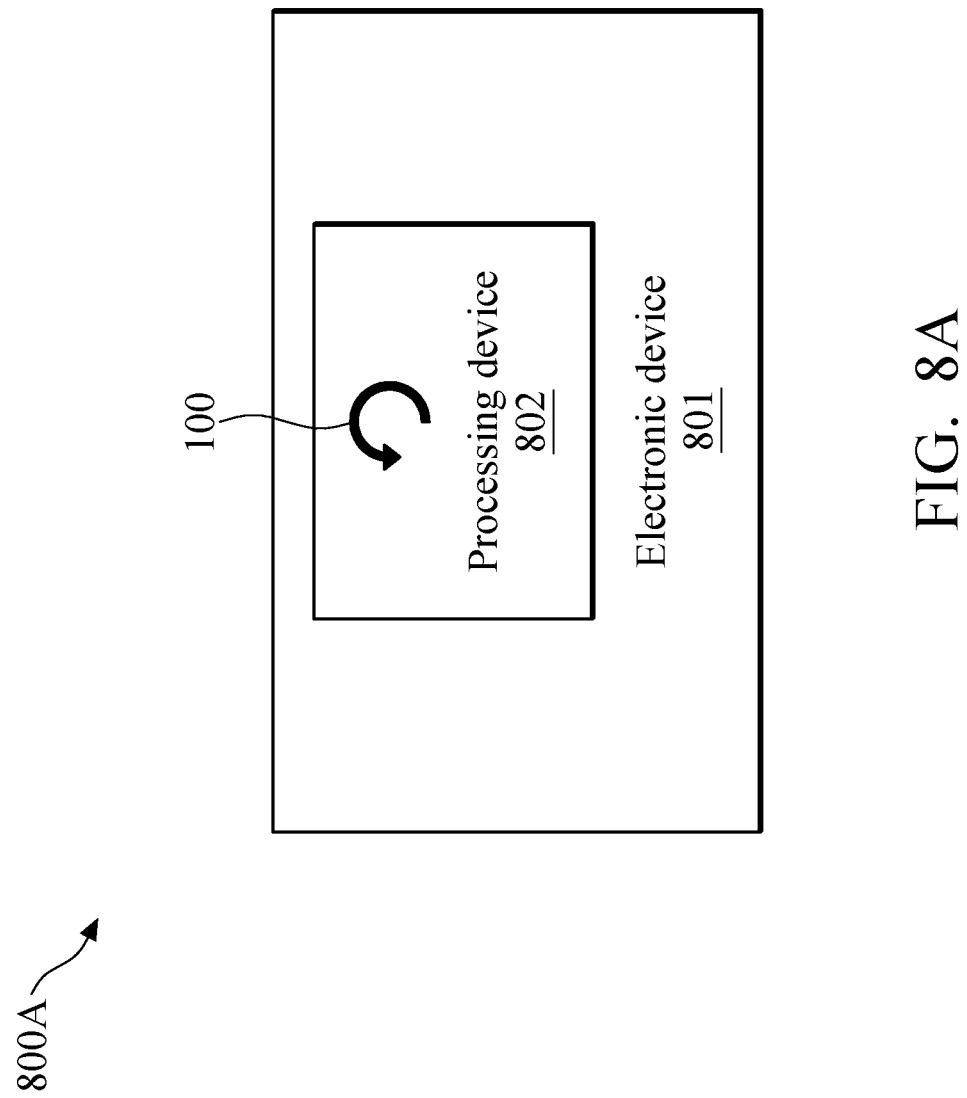
FIG. 8A-8C illustrate exemplary system architecture diagrams of a system for VCF detection in which the present application may be implemented.

FIG. 8A illustrates an exemplary system architecture diagram of a system 800A for VCF detection in which the present application may be implemented. As illustrated in FIG. 8A, system 800A for VCF detection includes an electronic device 801, and the electronic device 801 further includes a processing device 802 to load programs and perform the method 100 for VCF detection.

Figure 8B:
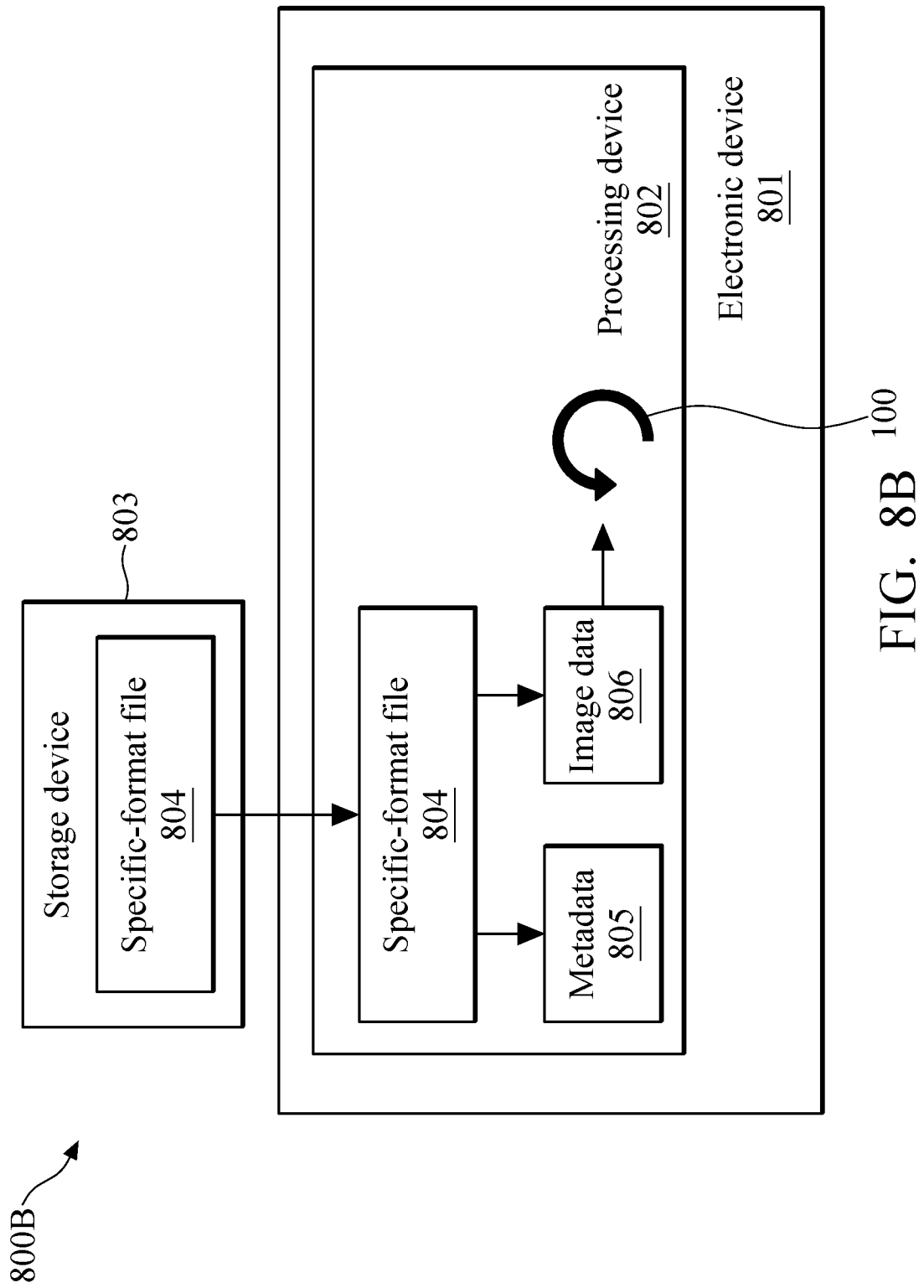

FIG. 8B is another exemplary system architecture diagram of another system 800B for VCF detection in which the present application may be implemented. As illustrated in FIG. 8B, in addition to the electronic device 801 as shown in FIG. 8A, system 800B for VCF detection further includes a storage device 803. Storage device 803 stores CT scans and patients' basic information as a specific-format file 804 and may transfer specific-format file 804 to electronic device 801. Electronic device 801 receives specific-format file 804 from storage device 803, and then deconstruct specific-format file 804 into a metadata 805 and an image data 806. Image data 806 is then used as an input of the VCF detection method 100.

In some embodiments, storage device 803 may be, for example, a hard drive protected with a security number, a computed tomography (CT) device, or a picture archiving and communication system (PACS).

In some embodiments, the file format of the specific-format file 804 is the Digital Imaging and Communications in Medicine (DICOM) format.

Figure 8C:
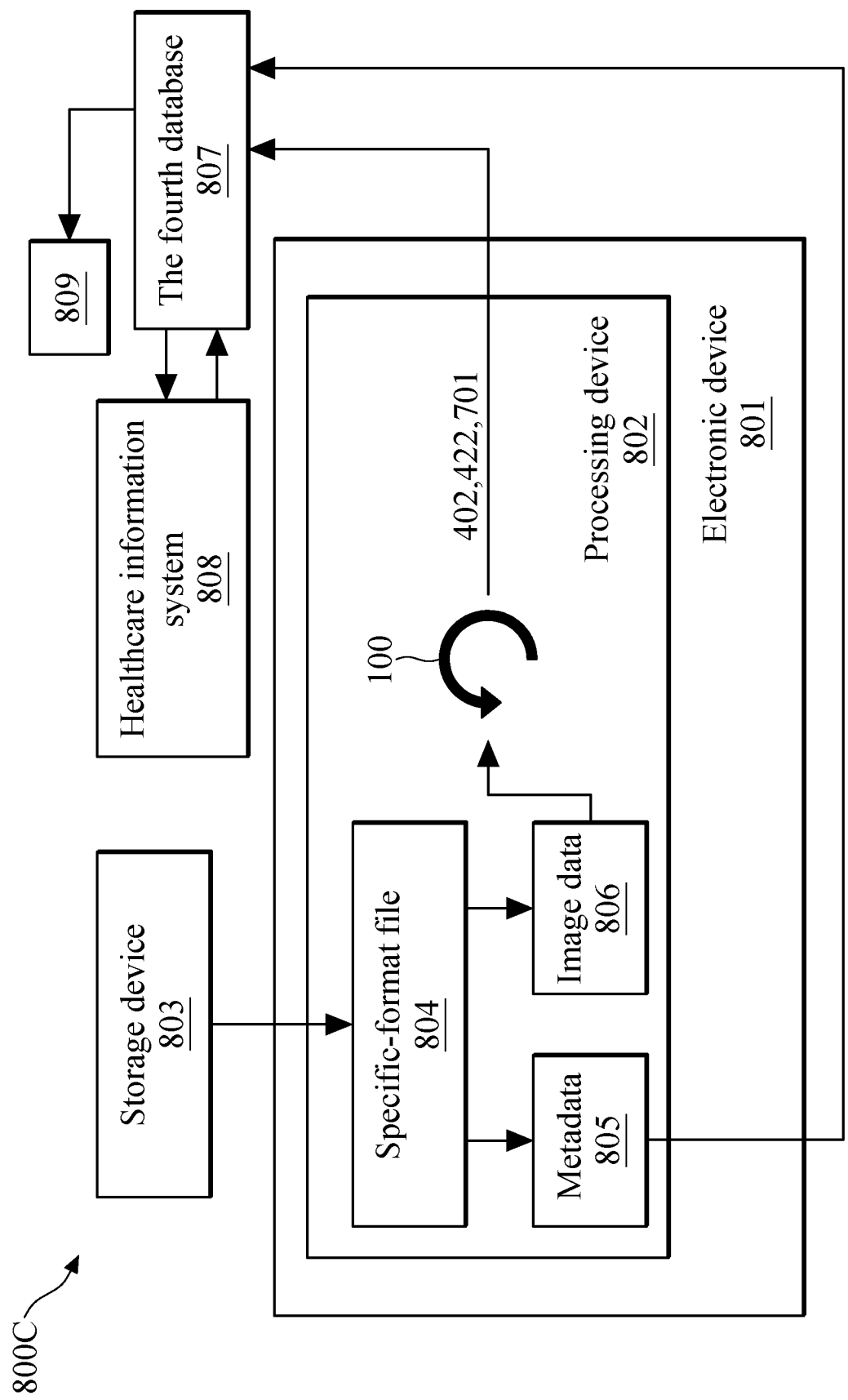

FIG. 8C is another exemplary system architecture diagram of another system 800C for VCF detection in which the present application may be implemented. As illustrated in FIG. 8C, in addition to the electronic device 801 and storage device 803 as shown in FIG. 8B, system 800C for VCF detection further includes the fourth database 807; the fourth database 807 may be saved to the electronic device 801 or another electronic device. As illustrated in FIG. 8C, detection result 402, localization result 602, and the corresponding ratio information, which are the output of the method 100 for VCF detection, may be written or updated to the fourth database 807 by electronic device 801.

In some embodiments, electronic device 801 uses a metadata parser to extract data fields in metadata 805, such as patients' name, gender, age, date of assessment, etc., then saves or updates these data fields to the fourth database 807.

In some embodiments, the electronic device 801 or another electronic device may access a healthcare information system 808 (e.g., a radiology information system (RIS)) for patients' medical records, extract the necessary information from the records via a search for the keywords appeared in the records, and write or update the extracted information to the fourth database 807.

In some embodiments, the system 800C for VCF detection may automatically create a report 809 for VCF detection with both medical images and the corresponding descriptions based on the content stored in the fourth database 807.

In some embodiments, processing device 802 in system 800A, system 800B and system 800C for VCF detection as described above may further perform a demonstration method to overlay the localization result and the evaluation result of compression fracture of each vertebral body into the sagittal reformatted images, and write or update the sagittal reformatted images with overlaid information to healthcare information system 808.

In some embodiments, processing device 802 in system 800A, system 800B and system 800C for VCF detection as described above further includes a display device (not shown in the Figures). The display device provides a user interface to demonstrate the sagittal reformatted image with localization result and the corresponding compression fracture grade, and allow medical domain professionals to revise the localization result of each vertebral body on the user interface.

Figure 9:
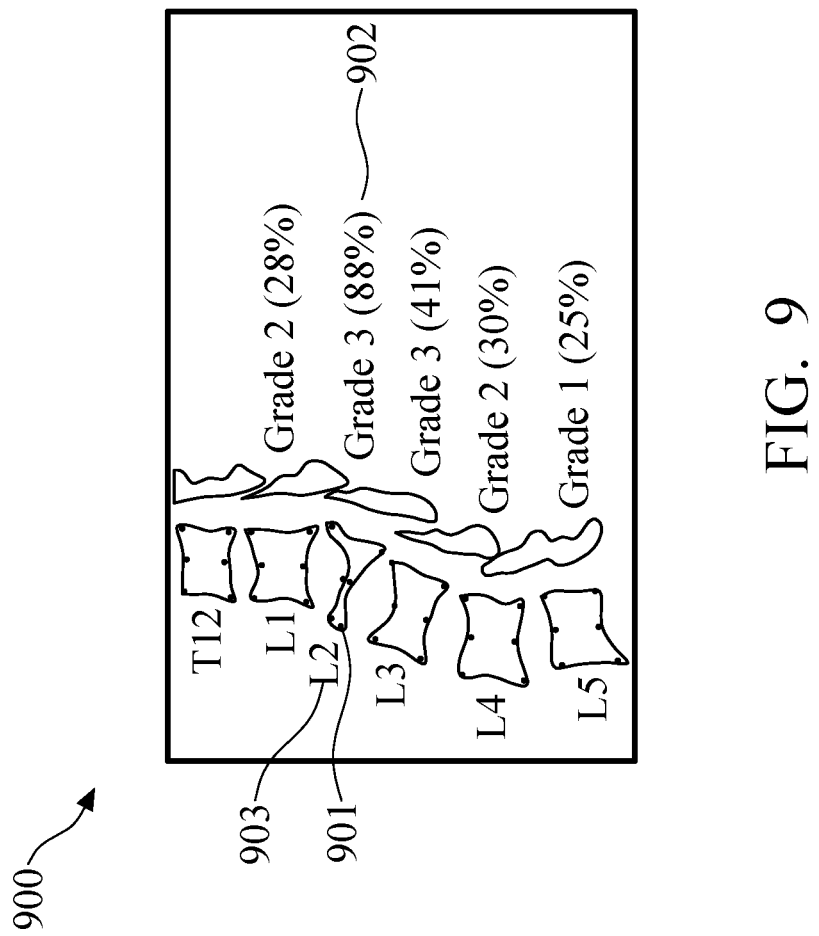
FIG. 9 illustrates an exemplary overlaid result that demonstrates the localization result of vertebral keypoints and evaluation result of the compression fracture grade for each vertebral body in a sagittal reformatted image.

FIG. 9 illustrates an exemplary overlaid result 900 that demonstrates the localization result of vertebral keypoints and evaluation result of the compression fracture grade for each vertebral body in a sagittal reformatted image. As illustrated in FIG. 9, the overlaid result 900 includes keypoints 901, a compression fracture grade 902, and vertebral name 903 for each vertebral body in a sagittal reformatted image. Compression fracture grade 902 includes the height-reduction ratios and the corresponding grades based on Genant's criteria described above of each vertebral body in the sagittal reformatted image. As illustrated by keypoints 901, a compression fracture grade 902 and vertebral name 903 in FIG. 9, in this embodiment, the height-reduction ratio of vertebral body L2 in the sagittal reformatted image is 88%, which is considered a Grade 3 (Severe) compression fracture.

In some embodiments, system 800A, system 800B and system 800C for VCF detection described above may be further configured to perform a joint-keypoint refinement method. The joint-keypoint refinement method is to use a trained deep-learning joint-keypoint refinement model to automatically refine the location of the rest of unrevised keypoints after either one or few keypoints of a vertebra are corrected manually by the medical domain professionals. And then, the corresponding compression fracture grade of the vertebral body in the sagittal reformatted image is updated, based on the refinement result of the trained deep-learning joint-keypoint refinement model.

For example, in an embodiment, if a medical domain professional revises the location of the anterior-superior keypoint of one vertebral body in a sagittal reformatted image on the user interface, then the system of VCF detection may feed the sagittal reformatted image which was revised by the medical domain professional into the trained deep-learning joint-keypoint refinement model. The trained deep-learning joint-keypoint refinement model then automatically refines the locations of the rest of five keypoints in the vertebral body which were not yet revised by the medical domain professional, i.e. the anterior-inferior keypoint, the middle-superior keypoint, the middle-inferior keypoint, the posterior-superior keypoint and the posterior-inferior keypoint. Then, the system of VCF detection calculate the corresponding compression fracture grade of the vertebral body based on the refinement result of the trained deep-learning joint-keypoint refinement model, and updates the corresponding compression fracture grade of the vertebral body to the overlaid result 900 on the sagittal reformatted image in FIG. 9.

Figure 10:
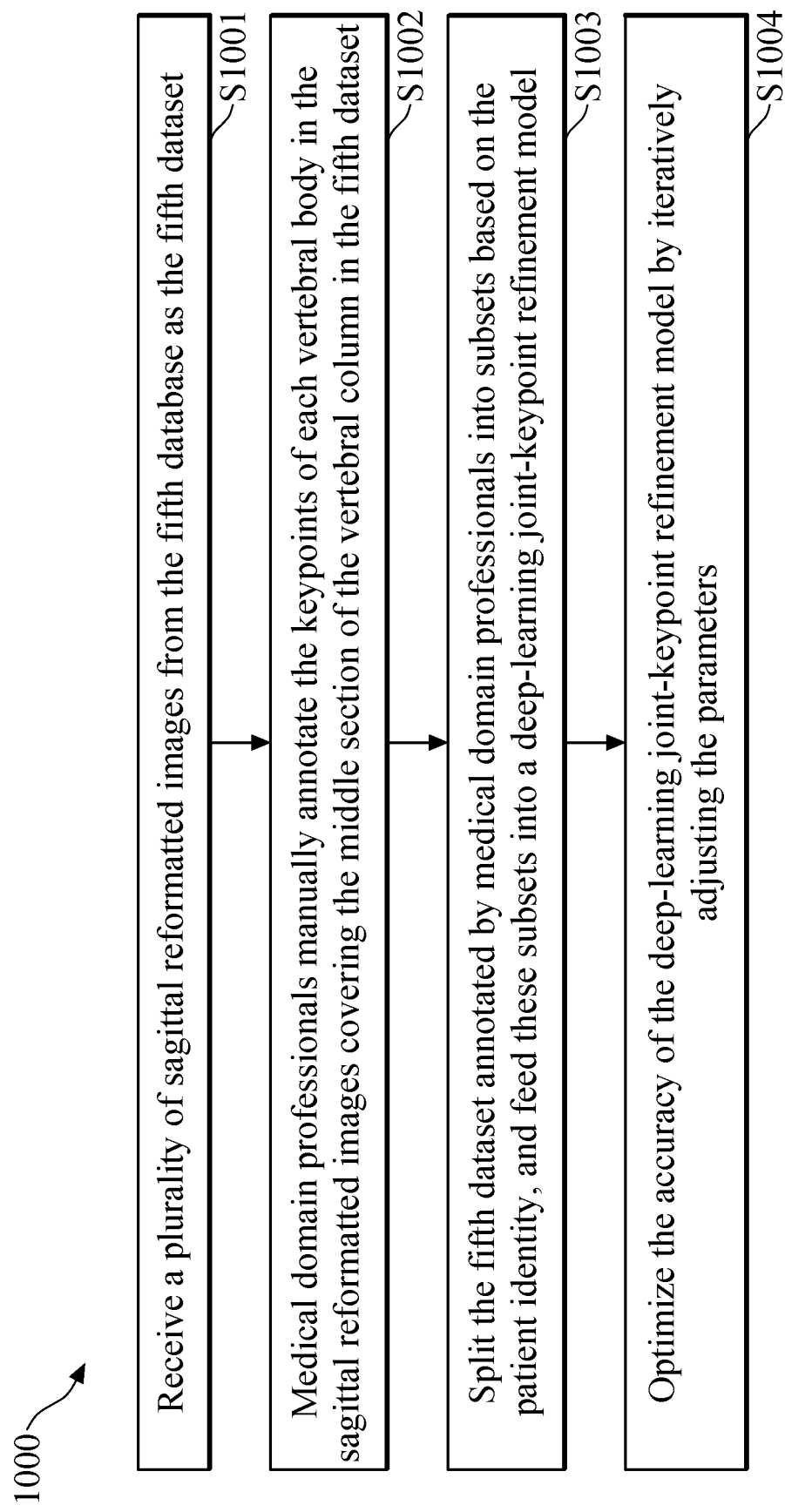
FIG. 10 is the flow diagram showing the training process of a deep-learning joint-keypoint refinement model, according to the embodiment of the present application.

FIG. 10 is the flow diagram showing the training process 1000 of the trained deep-learning joint-keypoint refinement model, according to the embodiment of the present application. The training process 1000 of the trained deep-learning joint-keypoint refinement model includes steps S1001-S2004. First, in step S1001, receive a plurality of sagittal reformatted image from the fifth database as the fifth dataset, and then perform step S1002. In step S1002, medical domain professionals manually annotate the keypoints of each vertebral body in the sagittal reformatted images covering the middle section of the vertebral column in the fifth dataset, and then perform step S1003. In step S1003, split the fifth dataset annotated by medical domain professionals into subsets based on the patient identity, and feed these subsets into a deep-learning joint-keypoint refinement model, and then perform step S1004. In step S1004, optimize the accuracy of the deep-learning joint-keypoint refinement model by iteratively adjusting the parameters; after performing the steps described above, generate the trained deep-learning joint-keypoint refinement model which is capable of refining the rest of keypoints of vertebral bodies based on the revised keypoint, and write or update the overlaid result 900 to healthcare information system 808.

In some embodiments, in step S1003, the deep-learning joint-keypoint refinement model is based on an Artificial Neural Network (ANN). The training process targets on minimizing the localization error between the keypoints localized by the model and the keypoints annotated by medical domain professionals, and the accuracy of the model is optimized through the iterative process of adjusting the model parameters.

The method and the system of VCF detection provided by the embodiments of the present invention may receive routine CT scans as input to evaluate and enumerate the severity of VCF on CT scans, thereby break through the limitations that performing image reformation manually on a CT scan console to obtain the optimal images for current clinical diagnosis of VCF, and support the clinical decision with quantitative results.

The order numbers in the specification and claims, such as "the first", "the second" and the like, are only for the convenience of describing. There are no chronological relationships between these order numbers.

The above paragraphs are described with multiple aspects. The teachings of the specification may be performed in multiple ways. Therefore, any specific structure or function disclosed in examples are only representative situations. According to the teachings of the specification, it is evident to those skilled in the art that any aspect disclosed may be performed individually, or that more than two aspects could be combined and performed.

While the invention has been described by way of example and in terms of the preferred embodiments, the invention is not limited to the disclosed embodiments. Rather, the invention is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of vertebral compression fracture detection, comprising:
    recombining a plurality of anatomical images captured in at least one spine segment of a target individual into a 3D image;
    using a multi-planar reconstruction method to reformat the 3D image to obtain at least one sagittal reformatted image;
    using a classification method to determine whether the sagittal reformatted image covers the middle section of a vertebral column or not;
    using a vertebral detection method to detect each vertebral body in the sagittal reformatted image covering the middle section of the vertebral column;
    using a keypoint localization method to localize a plurality of keypoints of each vertebral body which was detected in the sagittal reformatted image;
    measuring a plurality of vertebral heights based on the keypoints for each vertebral body; and
    evaluating the compression fracture grade of each vertebral body in the sagittal reformatted image based on the vertebral heights.

2. The method as claimed in claim 1, wherein the classification method uses a trained deep-learning classification model to determine whether the sagittal reformatted image covers the middle section of the vertebral column or not;
    wherein the input data required by the training process of the deep-learning classification model are a plurality of sagittal reformatted images with annotation indicating the middle or non-middle section of the vertebral column by medical domain professionals.

3. The method as claimed in claim 1, wherein the vertebral detection method uses a trained deep-learning detection model to detect each vertebral body in the sagittal reformatted image;
    wherein the input data required by the training process of the deep-learning detection model are a plurality of sagittal reformatted images in which the bounding box of each vertebral body is depicted by medical domain professionals.

4. The method as claimed in claim 1, wherein the keypoint localization method uses a trained deep-learning keypoint localization model to localize the keypoints of each vertebral body;
    wherein the input data required by the training process of the deep-learning keypoint localization model are a plurality of sagittal reformatted images in which the keypoints of each vertebral body are annotated by medical domain professionals.

5. A system of vertebral compression fracture detection, comprising:
    a computer, comprising a processor, for loading programs and performing the method as claimed in claim 1.

6. The system as claimed in claim 5, further comprising:
    a memory, storing CT scans and patients' basic information as a specific-format file, and transferring the specific-format file to the computer;
    the computer receives the specific-format file from the memory, deconstructs the specific-format file into metadata and image data, and uses the image data as input to perform the method as claimed in claim 1.

7. The system as claimed in claim 5, wherein the processor further performs a demonstration method to overlay the localization result of the vertebral keypoints and the evaluation result of the compression fracture grade for each vertebral body in the sagittal reformatted image.

8. The system as claimed in claim 7, further comprising:
    a display, providing a user interface to demonstrate the sagittal reformatted image overlaid with the localization result and the corresponding compression fracture grade for each vertebral body, and allow medical domain professionals to revise the localization result for each vertebral body on the user interface.

9. The system as claimed in claim 8, wherein the processor further performs a joint-keypoint refinement method, and is configured to:
    use a trained deep-learning joint-keypoint refinement model to automatically refine the location of the rest of unrevised keypoints after either one or few keypoints of a vertebra are corrected manually by the medical domain professionals;
    update the corresponding compression fracture grade of the vertebral body in the sagittal reformatted image, based on the result of the trained deep-learning joint-keypoint refinement model;
    wherein the input data required by the training process of the deep-learning joint-keypoint refinement model are a plurality of sagittal reformatted images in which the keypoints of each vertebral body are annotated by medical domain professionals.

* * * * *